(12) United States Patent
Sheena et al.

(10) Patent No.: US 8,957,095 B2
(45) Date of Patent: Feb. 17, 2015

(54) TREATMENT OF SUNBURN USING ANALGESICS AND ANTIHISTAMINES

(75) Inventors: Talal Sheena, Jamul, CA (US); Melwyn Abreo, Jamul, CA (US)

(73) Assignee: Sephoris Pharmaceuticals, LLC, Jamul, CA (US)

( * ) Notice: Subject to any disclaimer, the term of this patent is extended or adjusted under 35 U.S.C. 154(b) by 0 days.

(21) Appl. No.: 13/504,084

(22) PCT Filed: Oct. 26, 2010

(86) PCT No.: PCT/US2010/054157
§ 371 (c)(1),
(2), (4) Date: May 24, 2012

(87) PCT Pub. No.: WO2011/056604
PCT Pub. Date: May 12, 2011

(65) Prior Publication Data
US 2012/0225914 A1    Sep. 6, 2012

Related U.S. Application Data

(60) Provisional application No. 61/254,803, filed on Oct. 26, 2009.

(51) Int. Cl.
| | |
|---|---|
| *A61K 31/135* | (2006.01) |
| *A61K 31/192* | (2006.01) |
| *A61K 31/435* | (2006.01) |
| *A61K 31/4402* | (2006.01) |
| *A61K 31/444* | (2006.01) |
| *A61K 31/495* | (2006.01) |
| *A61K 31/5415* | (2006.01) |
| *A61K 31/554* | (2006.01) |
| *A61K 31/60* | (2006.01) |
| *A61K 45/06* | (2006.01) |

(52) U.S. Cl.
CPC ............ *A61K 31/135* (2013.01); *A61K 31/192* (2013.01); *A61K 31/435* (2013.01); *A61K 31/4402* (2013.01); *A61K 31/444* (2013.01); *A61K 31/495* (2013.01); *A61K 31/5415* (2013.01); *A61K 31/554* (2013.01); *A61K 31/60* (2013.01); *A61K 45/06* (2013.01)
USPC ........................................................ 514/357

(58) Field of Classification Search
USPC ........................................................ 514/357
See application file for complete search history.

(56) References Cited

U.S. PATENT DOCUMENTS

| | | | |
|---|---|---|---|
| 3,278,379 A | 10/1966 | Mansor | |
| 4,619,934 A | 10/1986 | Sunshine et al. | |
| 5,100,918 A | 3/1992 | Sunshine | |
| 5,993,833 A | 11/1999 | De Lacharriere et al. | |
| 2003/0129209 A1 | 7/2003 | Walch | |
| 2005/0074414 A1 | 4/2005 | Tamarkin et al. | |
| 2005/0192355 A1 | 9/2005 | Berlin | |
| 2007/0014757 A1* | 1/2007 | Chauhan et al. | ........... 424/78.27 |
| 2007/0134493 A1 | 6/2007 | Meghpara | |
| 2007/0148238 A1 | 6/2007 | Nangia et al. | |
| 2008/0113021 A1 | 5/2008 | Shen | |
| 2008/0312168 A1 | 12/2008 | Pilgaonkar et al. | |
| 2008/0317684 A1 | 12/2008 | Spann-Wade et al. | |
| 2009/0004248 A1 | 1/2009 | Bunick et al. | |
| 2009/0196840 A1 | 8/2009 | Lorenzo | |

FOREIGN PATENT DOCUMENTS

| | | |
|---|---|---|
| EP | 1284151 A1 | 2/2003 |
| JP | 11193230 A | 1/2000 |
| WO | 92/05783 A1 | 4/1992 |
| WO | 95/07103 A1 | 3/1995 |
| WO | 97/34585 A1 | 9/1997 |
| WO | 99/45921 A1 | 9/1999 |
| WO | 01/87236 A2 | 11/2001 |
| WO | 2005/009342 A2 | 2/2005 |
| WO | 2005/046727 A2 | 5/2005 |
| WO | 2005/079272 A2 | 9/2005 |
| WO | 2008/117018 A2 | 10/2008 |
| WO | 2009/145921 A1 | 12/2009 |

OTHER PUBLICATIONS

Han et al., Management of Acute Sunburn, Am J Clin Dermatol; 5(1):39-47, 2004.*
Nicholson et al., Sedation and histamine H1-receptor antagonism: studies in man with the enantiomers of chlorpheniramine and dimethindene, Br. J. Pharmacol. 104, 270-276, 1991.*
Ceschel et al., Design and Evaluation of a New Transdermal Formulation Containing Chlorpheniramine Maleate, Drug Development and Industrial Pharmacy, 25(9), 1035-1039, 1999.*
Kotzan et al., Bioavailability of Regular and Controlled-Release Chlorpheniramine Products, Journal of Pharmaceutical Sciences, 71(8), 919-923, 1982.*
Jens-Uwe Grundmann et al., "UV Erythema Reducing Capacity of Mizolastine Compared to Acetyl-salicylic Acid or Both Combined in Comparison to Indomethacin+", Photochemistry and Photobiology, vol. 74, No. 4, Oct. 1, 2001, pp. 587-592, XP55032598, ISSN: 0031-8655, DOI: 10.1562/0031-8655(2001)0740587UERCOM2.0.CO2.
Nakashima et al., "Antihistaminic and anti-inflamatory effects of Epiamart[rho] S by topical application", Database Embase [Online] Elsevier Science Publishers, Amsterdam, NL, 1996, XP002679915, Database accession No. EMB-1997296761; & Nakashima et al., "Antihistaminic and anti-inflamatory effets of Epiamart[rho] S by topical application," Japanese Pharmacology and Therapeutics 1996 JP, vol. 24, No. 10, 1996, pp. 91-95, ISSN: 0386-3603.

(Continued)

*Primary Examiner* — Jefferey S Lundgren
*Assistant Examiner* — Zenab Olabowale
(74) *Attorney, Agent, or Firm* — Kilpatrick Townsend & Stockton LLP

(57) ABSTRACT

Combination compositions and kits comprising an analgesic and an antihistamine are provided as well as methods of use in treating sunburn.

6 Claims, 5 Drawing Sheets

(56) References Cited

OTHER PUBLICATIONS

Search Report and Written Opinion mailed Jul. 28, 2011 in related PCT Application No. PCT/US2010/054157, filed Oct. 26, 2010, 8 pages.

Search Report mailed Jul. 23, 2012 in related European Patent Application No. 10828865.5, filed Oct. 26, 2010, 13 pages.

Akter et al., Effects of Several Agents on UVB- and UVA Plus Systemic Fluoroquinolone-Induced Erythema of Guniea Pig Skin Evaluated by Reflectance Colorimetry, Free Radical Biology & Medicine, vol. 24, No. 7/8 pp. 1113-1119, 1998, 7 pages.

Eaglstein et al., Ultraviolet Irradiation-Induced Inflammation, Effects of Steroid and Nonsteroid Anti-inflammatory Agents, Dec. 1979, 3 pages.

E.K. Edwards and E.K. Edwards, "The effect of antihistamines on ultraviolet-light-induced erythema", Int. J. Dermatol., 1983, 22, 540-541.

Ikai et al., Ear swelling in response to UVB irradiation, Arch Dermatol Res (1986) 278 : 445-448, 4 pages.

Kienzler et al., Diclofenac-Na Gel Is Effective in Reducing the Pain and Inflammation Associated with Exposure to Ultraviloet Light—Results of Two Clinical Studies, Skin Pharmacol Physiol 2005;18:144-152, 9 pages.

Magnette et al., The efficacy and safety of low-dose diclofenacsodium 0.1% gel for the symptomatic relief of pain and erythema associated with superficial natural sunburn, Eur J Dermatol 2004; 238-46, 9 pages.

Miller et al., Aspirin and Ultraviolet Light-Induced Erythema in Man, Arch Derm—vol. 95, Apr. 1967, 2 pages.

Snowise et al., Cold, Wind, and Sun Exposure Managing- and Preventing-Skin Damage, vol. 32 • No. 12 • Dec. 2004, The Physician and Sportsmedicine, 7 pages.

Stern et al., Ibuprofen in the Treatment of UV-B-Induced Inflammation, Arch Dermatol—vol. 121, Apr. 1985, 5 pages.

Yan et al., Inhibitory Effects of Mizolastine on Ultraviolet B-Induced Leukotriene B4 Production and 5-Lipoxgenase Expression in Normal Human Dermal Fibroblasts In Vitro, Photochemistry and Photobiology, 2006, 82: 665-669, 5 pages.

Yourick et al., Reduction of Erythema in Hairless Guinea Pigs after Cutaneous Sulfur Mustard Vapor Exposure by Pretreatment with Niacinamide, Promethazine and Indomethacin*, Journal of Applied Toxicology, vol. 15(2), 133-138 (1995), 6 pages.

A. Han and H.I. Maibach, "Management of acute sunburn", Am. J. Clin. Dermatol., 2004, 5(1), 39-47.

Edward K. Edwards, Jr., Stephen N. Horwitz, and Phillip Frost, "Reduction of the Erythema Response to Ultraviolet Light by Nonsteroidal Antiinflammatory Agents", Arch Dermatol Res (1982) 272:263-267.

* cited by examiner

Fig. 1A
Fig. 1B
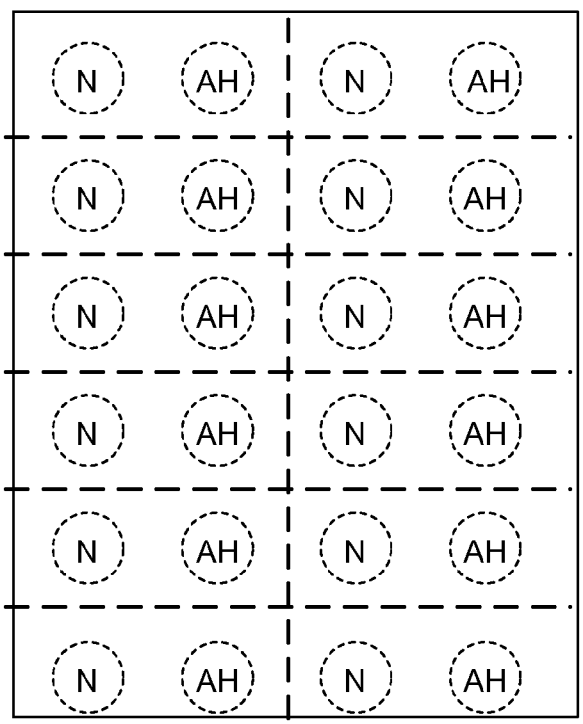
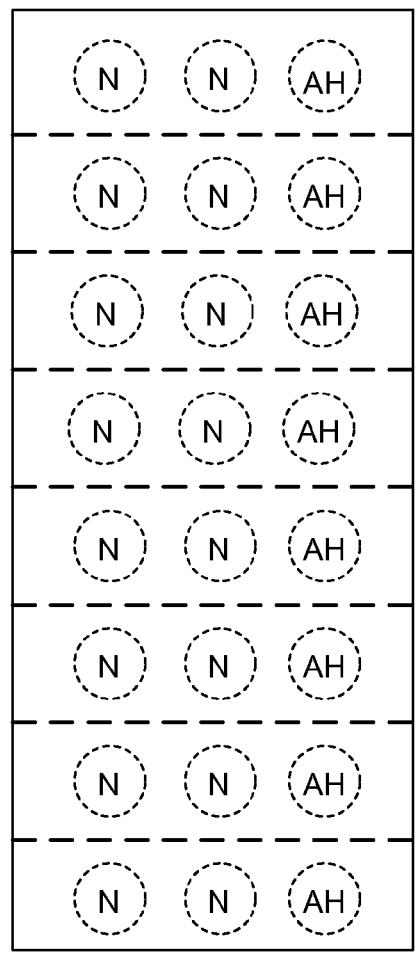

Fig. 4

|  | DAY 1 | | | | DAY 2 | | |
|---|---|---|---|---|---|---|---|
| Dose 1 | (N) | (AH) | (N') | Dose 1 | (N) | (AH) | (N') |
| Dose 2 | (N) | (AH) | (N') | Dose 2 | (N) | (AH) | (N') |
| Dose 3 | (N) | (AH) | (N') | Dose 3 | (N) | (AH) | (N') |
| Dose 4 | (N) | (AH) | (N') | Dose 4 | (N) | (AH) | (N') |
|  | DAY 3 | | | | DAY 4 | | |
| Dose 1 | (N) | (AH) | (N') | Dose 1 | (N) | (AH) | (N') |
| Dose 2 | (N) | (AH) | (N') | Dose 2 | (N) | (AH) | (N') |
| Dose 3 | (N) | (AH) | (N') | Dose 3 | (N) | (AH) | (N') |
| Dose 4 | (N) | (AH) | (N') | Dose 4 | (N) | (AH) | (N') |

TREATMENT OF SUNBURN USING ANALGESICS AND ANTIHISTAMINES

CROSS-REFERENCES TO RELATED APPLICATIONS

This application is a national stage of PCT/US2010/054157, filed Oct. 26, 2010, which claims the benefit of U.S. Provisional Application No. 61/254,803, filed Oct. 26, 2009, incorporated herein by reference in its entirety and for all purposes.

BACKGROUND OF THE INVENTION

Sunburn is a burn to the skin caused by ultraviolet (UV) radiation. Extended UV exposure can also lead to skin cancer. Sunburn often manifests with one or more of the following symptoms: erythema (redness), pain, edema (swelling), itching, peeling, rash, warmth, nausea, headache, and fever. More severe sunburns can also cause blistering.

Available remedies for minor sunburn include topical anesthetics, such as benzocaine, or topical wound care agents, such as aloe vera. Existing remedies, however, fail to adequately treat sunburns and the associated symptoms thereof. Sunburn is a very common malady for which there is no FDA approved therapy. Current data suggest that about 36% of all U.S. adults experience one or more sunburns each year. Thus, there is a need in the art for effective medications for the treatment of sunburns. The present invention meets these and other needs in the art.

BRIEF SUMMARY OF THE INVENTION

The present inventors have discovered that the combination of an analgesic (e.g. an NSAID or over-the-counter analgesic) and an antihistamine is effective to treat sunburn. The combination composition provides a safe, effective, and convenient treatment for sunburn.

In one aspect, a method of treating a sunburn in a subject (e.g. a human subject) in need of such treatment is provided. The method includes administering to the subject a combined therapeutically effective amount of an analgesic (e.g. over-the-counter analgesic) and an antihistamine.

In another aspect, a kit is provided for the treatment of a sunburn (e.g. of a human). The kit includes a dispensing apparatus having a plurality of analgesic dosage units and a plurality of antihistamine dosage units.

In another aspect, a combination composition product for treatment of a sunburn (of a human) in a subject in need such treatment is provided. The combination composition product includes effective amounts of an analgesic (e.g. over-the-counter analgesic) and an antihistamine.

BRIEF DESCRIPTION OF THE DRAWINGS

The drawings are provided for demonstrative purposes only and are not necessarily drawn to scale. No attempt is made to show structural features in more detail than may be necessary for a fundamental understanding of the invention. For ease of demonstration, the analgesic (e.g., an NSAID) is designated "N", the antihistamine is designated "AH," and the combination of an analgesic and an antihistamine is designated "NAH."

FIGS. 1A-1B depict exemplary dispensers having a row-and-column configuration with analgesic blisters and antihistamine blisters. FIG. 1A depicts a configuration wherein each dose, indicated by perforations, includes one analgesic dosage unit and one antihistamine dosage unit. FIG. 1B depicts a configuration wherein each dose, indicated by perforations, includes more than one analgesic dosage unit and one antihistamine dosage unit.

FIG. 2A depicts combination blisters containing co-formulated analgesic and antihistamine. FIG. 2B depicts combination blisters including a partition separating individually formulated active agents. FIG. 2C depicts a snap-lid type dispenser apparatus configured to dispense individually formulated active agents.

FIG. 4 depicts an exemplary dispenser configuration featuring QID dosing of an analgesic and an antihistamine for 4 days. After each combination dose, a follow up dose of analgesic (N') may be administered.

DETAILED DESCRIPTION OF THE INVENTION

I. Definitions

Figure 2A:
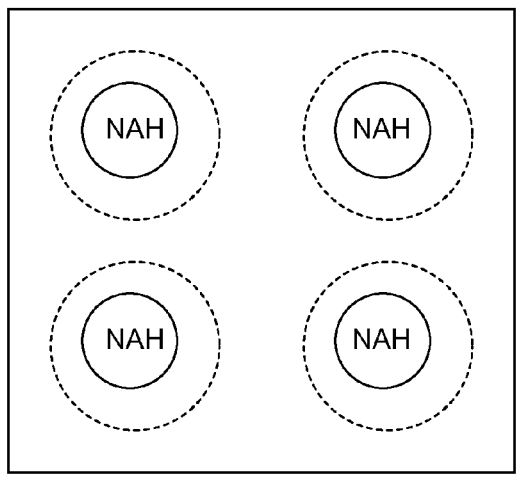
FIGS. 2A-2C depict exemplary dispenser apparatuses configured to eject both active agents at once.

In some embodiments, the composition is used to treat a disease, e.g., a sunburn such as an acute sunburn. "Treating" the disease includes one or more of: addressing a physiological cause of the disease, addressing a physiological cause of a disease symptom, reducing the severity of the disease, ameliorating a symptom of the disease, and shortening the duration of the disease (e.g. decreasing recovery time from a sunburn). Therefore, treating a sunburn includes relief (e.g. temporary relief) of pain or discomfort due to mild to moderate sunburn and relief (e.g. temporary relief) of redness due to mild or moderate sunburn.

The "subject" as used herein is a subject in need of treatment for sunburn. The subject is preferably a human, but also may include laboratory, pet, domestic, or livestock animals. In one embodiment, the subject is a mammal having at least some portion of exposed or partially exposed skin that is not completely shielded from radiation by hair (such as a human or a hairless rat, mouse, or dog).

The term "combined therapeutically effective amount" means that the active agents, when co-administered, are effective to treat sunburn. The amount of one active agent may be insufficient to treat a sunburn in the absence of the second active agent, but together they are therapeutically effective.

The term "individually therapeutically effective amount" means an amount of a single active agent that, when administered, is effective to treat sunburn. The efficacy of an individually effective amount of an active agent can be supplemented with, or synergistically enhanced by, the addition of the second active agent. The second active agent may be administered in an individually therapeutically effective amount or as part of a combined therapeutically effective amount.

The term "substantially free" means that the specified component is either entirely absent, or it is present in an amount too small to contribute to therapeutic efficacy, either alone or in combination with the other active agents.

The term "co-administer" means to administer more than one active agent, such that the duration of physiological effect of one active agent overlaps with the physiological effect of a second active agent. For systemic agents, the term co-administer means that more than one active agent is present in the bloodstream during at least one time point. In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single dosage unit including both active agents. In other embodiments, the active agents can be formulated separately. In some embodiments, each active agent is formulated separately, but administered approximately simultaneously.

A "dosage unit" is a discrete item for administration, such as a tablet or capsule. For a liquid dosage form, the dosage unit may be, e.g., a teaspoon, tablespoon, or dosing cup amount of the liquid formulation.

The term "dose" is the amount of active agent to be administered at one time. The dose may be present in a single dosage unit, or it may be divided among more than one dosage unit. For example, a dose of 400 mg ibuprofen may be administered as a single 400 mg tablet, or it may be administered as two 200 mg tablets.

The "daily dose" is the amount of active agent that is to be administered per day (i.e., any 24 hour period). The daily dose can include one or more doses. For example, a daily dose of 600 mg ibuprofen can be administered as a single 600 mg dose, or three 200 mg doses.

The "treatment dose" is the amount of active agent that is to be administered during a course of treatment. The treatment dose may include one or more doses that may be the same as or different from one another. For example, the treatment regimen may include a titration period of increasing doses and/or a weaning period of decreasing doses.

The term "and/or" as used herein indicates that one or more of the stated cases may occur.

II. Combination Compositions

A. Active Agents

Provided herein are combination compositions including an analgesic (e.g. over-the-counter (OTC) analgesic) and an antihistamine. The analgesic and antihistamine may be co-formulated to form at least a portion of a single dosage unit, or they may be individually formulated to form separate dosage units. The combination composition may be formulated for oral administration. The combination compositions are particularly useful for treating sunburn as described in detail further below.

Unless otherwise noted, the analgesic (e.g. OTC analgesic) and/or the antihistamine active agents may be present as free agents or as a pharmaceutically acceptable salts. For example, chlorpheniramine may be present as a maleate salt.

An analgesic is a pain-relieving active agent, such as acetaminophen or an NSAID. An over-the-counter (OTC) analgesic is an analgesic available, for at least one dose strength, without a prescription. In particular, an OTC analgesic is any pain-relieving active agent that, for at least one dose strength, is approved by the U.S. Food and Drug Administration prior to Oct. 26, 2009 for administration without a prescription from a health care professional. The OTC analgesic can be, for example, acetaminophen (paracetamol, APAP) or a non-steroidal anti-inflammatory drug (NSAID) such as ibuprofen.

In one embodiment, the analgesic is an NSAID. In some embodiments, the NSAID is an OTC NSAID. An NSAID is a non-steroidal anti-inflammatory drug. An NSAID typically has analgesic, antipyretic, and/or anti-inflammatory effects. Acceptable NSAIDs include, but are not limited to: an ibuprofen, an aspirin, a naproxen, a diclofenac, a licofelone, omega-3 fatty acids, a COX-2 inhibitor (e.g., celecoxib), a sulphonanilide (e.g., nimesulide), an indomethacin, and combinations thereof. In some embodiments, the NSAID is an aspirin, an ibuprofen, or a naproxen. In some embodiments, the NSAID is an ibuprofen. In another embodiment, the NSAID is racemic ibuprofen (i.e., (S)- and (R)-ibuprofen).

An antihistamine is an agent that inhibits the release or action of histamine. Useful antihistamines include, but are not limited to, $H_1$-receptor antagonists and/or $H_2$-receptor antagonists. In some embodiments, the $H_1$-receptor antagonist is a chlorpheniramine, a diphenhydramine, a loratadine, a desloratadine, a meclizine, a quetiapine, a fexofenadine, a pheniramine, a cetirizine, a promethazine, and a levocetirizine. Useful $H_2$-receptor antagonists may include a cimetidine, a famotidine, a ranitidine, a nizatidine, a roxatidine, or a lafutidine, and combinations thereof. In some embodiments, the antihistamine is an $H_1$-receptor antagonist. In some embodiments, the antihistamine is a chlorpheniramine.

In some embodiments, the antihistamine is chlorpheniramine, and the analgesic is an NSAID. In related embodiments, the antihistamine is chlorpheniramine, and the analgesic is an ibuprofen. In one embodiment, the antihistamine is a chlorpheniramine, and the analgesic is a racemic ibuprofen.

In some embodiments, the combination composition is substantially free of any additional active agent not specifically recited. For example, in some embodiments where the combination composition is stated to include chlorpheniramine and ibuprofen, the composition is substantially free of any additional active agents. In certain embodiments, the combination composition is substantially free of any additional oral active agent not specifically recited. In other embodiments, the combination composition is substantially free of any additional synthetic active agent (i.e., an active agent that is not found in nature, but rather is made synthetically) not specifically recited. In another embodiment, the combination composition is substantially free of any additional active agent used for treating sinus symptoms (e.g., cold, flu, or allergy symptoms). Such active agents useful for treating sinus symptoms that may be excluded for the combination compositions provided herein include decongestants (e.g., pseudoephedrine, phenylephrine, phenylpropanolamine, oxymetazoline), steroids (e.g., cortisone, dexamethasone, hydrocortisone, prednisone), epinephrine, theophylline, anti-tussives (e.g., opiates such as codeine, dextromethorphan), expectorants (e.g., guaifenesin), anti-leukotrienes (e.g., montelukast), anti-cholinergics (e.g., ipratropium, oxitropium, tiotropium), and mast cell stabilizers (e.g., cromolyn and nedocromil). In some embodiments, the combination composition is substantially free of pseudoephedrine.

In another embodiment, the combination composition may include one or more additional active agents (i.e. agents other than the recited analgesic and antihistamine). In one embodiment, the one or more additional active agent is administered topically. In one embodiment, the combination composition includes an additional active agent useful for treating burns. Exemplary additional active agents include topical anesthetics (e.g., benzocaine, lidocaine), topical wound care agents (e.g., aloe), topical anti-pruritic agents (e.g., calamine), topical moisturizers (e.g., vitamin E, dimethicone, oatmeal), topical debriding agents, and topical or systemic anti-infectives (e.g., antibacterial agents, antifungal agents, silver sulfadiazine, bacitracin, neomycin, polymyxin B, aminoglycosides). In one embodiment, the additional active agent is a natural active agent such as oatmeal or aloe. In certain embodiments, a single additional active agent is present (and no other active agents are present). In other embodiments, two additional active agents are present (and no other active agents are present). In other embodiments, three additional active agents are present (and no other active agents are present). In other embodiments, four additional active agents are present (and no other active agents are present). In other embodiments, five additional active agents are present (and no other active agents are present).

In another embodiment, there is provided a combination composition product (e.g. an oral combination composition product, parenteral combination composition product or a topical composition product) for treatment of a sunburn in a subject in need of such treatment. The combination composition product includes: (i) 16-20 analgesic dosage units (e.g. an oral analgesic dosage units, parenteral analgesic dosage units or topical analgesic dosage units) and 16-20 antihistamine dosage units (e.g. an oral antihistamine dosage units, parenteral antihistamine dosage units or topical antihistamine dosage units). In some embodiments the combination product includes: (i) 16-20 ibuprofen dosage units (e.g. an oral ibuprofen dosage units, parenteral ibuprofen dosage units or topical ibuprofen dosage units), each containing about 50 mg to about 800 mg of ibuprofen (or other specific dosages described below), or a pharmaceutically acceptable salt thereof; and (ii) 16-20 chlorpheniramine dosage units (e.g. an oral chlorpheniramine dosage units, parenteral chlorpheniramine dosage units or topical chlorpheniramine dosage units), each containing about 50 mg to about 800 mg of ibuprofen (or other specific dosages described below), each containing about 1 mg to about 8 mg of chlorpheniramine (or other specific dosages described below), or a pharmaceutically acceptable salt thereof. The dosage units may be suitable for administering 2-6 times (e.g. 3, 4 or 5 times) per day. The analgesic (e.g. ibuprofen) dosage units and the antihistamine (e.g. chlorpheniramine) dosage units may be substantially free of additional active agents (e.g. synthetic active agent). In some embodiments, the dosage units are oral dosage units. In certain embodiments, 16, 17, 18, 19 or 20 dosage units are provided.

In one embodiment, there is provided a combination composition product (e.g. an oral combination composition product, parenteral combination composition product or a topical composition product) for treatment of a sunburn in a subject in need such treatment. The combination composition product includes 16-20 dosage units, each containing an analgesic (e.g. NSAID) and an antihistamine. In some embodiments, the combination composition product includes 16-20 dosage units, each containing about 50 mg to about 800 mg of ibuprofen (or other specific dosages described below) and about 1 mg to about 8 mg of chlorpheniramine (or other specific dosages described below). The dosage units are suitable for administering 3-6 times per day (e.g. 4 or 5). In some embodiments, each of the dosage units are substantially free of additional active agents (e.g. synthetic active agents). In some embodiments, the dosage units are oral dosage units. In certain embodiments, 16, 17, 18, 19 or 20 antihistamine and/or analgesic dosage units are provided.

In one embodiment, there is provided a combination composition product (e.g. an oral combination composition product, parenteral combination composition product or a topical composition product) for treatment of a sunburn in a subject in need of such treatment. The combination product includes a minimum of 3 and a maximum of 40 dosage units. Each dosage unit comprises an analgesic (e.g. NSAID) dose and an antihistamine dose. In some embodiments, each of the dosage units are substantially free of additional active agents (e.g. synthetic active agents). In some embodiments, the dosage units are oral dosage units. In certain embodiments, 5-35 dosage units, 10-30, 15-25 or about 20 dosage units are provided. In certain embodiments, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 dosage units are provided.

In one embodiment, there is provided a combination composition product (e.g. an oral combination composition product, parenteral combination composition product or a topical composition product) for treatment of a sunburn in a subject in need of such treatment. The combination product includes a minimum of 3 and a maximum of 40 analgesic (e.g. NSAID) dosage units. In some embodiments, each analgesic (e.g. NSAID) dosage unit includes a dose of a ibuprofen. Also included is a minimum of 3 and a maximum of 40 antihistamine dosage units. In some embodiments, antihistamine dosage unit includes a dose of an chlorpheniramine. In some embodiments, the analgesic and antihistamine dosage units are substantially free of additional active agents (e.g. synthetic active agents). In some embodiments, the dosage units are oral dosage units. In certain embodiments, 5-35 antihistamine and/or analgesic dosage units, 10-30, 15-25 or about 20 dosage units are provided. In certain embodiments, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 antihistamine and/or analgesic dosage units are provided.

In one embodiment, the combination composition product (e.g. an oral combination composition product, parenteral combination composition product or a topical composition product) includes: (i) a minimum of 4 and a maximum of 32 analgesic (e.g. NSAID) dosage units; and a minimum of 4 and a maximum of 16 antihistamine dosage units. In some embodiments, the dosage units are oral dosage units. In certain embodiments, 10-30, 15-25 or about 20 analgesic dosage units are provided. In certain embodiments, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 analgesic dosage units are provided. In some embodiments, 4, 5, 6, 7, 8, 9, 10, 11, 12, 13, 14, 15, or 16 antihistamine dosage units are provide (e.g. 8-12, about 10 or about 14). In some embodiments, the analgesic and antihistamine dosage units are substantially free of additional active agents (e.g. synthetic active agents).

In another embodiment, the combination composition product (e.g. an oral combination composition product, parenteral combination composition product or a topical composition product) contains: (i) a minimum of 4 and a maximum of 16 first analgesic (e.g. NSAID) dosage units. In some embodiments, each first analgesic dosage unites comprises about 200 mg ibuprofen. The combination composition product also includes a minimum of 4 and a maximum of 16 antihistamine dosage units. In some embodiments, each antihistamine dosage unit comprises 2-4 mg chlorpheniramine. The combination composition product also includes a minimum of 4 and a maximum of 16 second analgesic (e.g. NSAID) dosage units, wherein each of the second analgesic dosage units have less analgesic than each of the first analgesic dosage unites. In some embodiments, each of the second analgesic dosage units include about 100 mg ibuprofen. In some embodiments, the dosage units are oral dosage units. In some embodiments, 4, 5, 6, 7, 8, 9, 10, 11, 12, 13, 14, 15, or 16 each of the dosage units are provide (e.g. 8-12, about 10 or about 14). In some embodiments, each of the dosage units are substantially free of additional active agents (e.g. synthetic active agents). In some embodiments, the dosage units are oral dosage units.

In some embodiments of the combination compositions provided herein, the NSAID is an aspirin, an ibuprofen, a naproxen, or a pharmaceutically acceptable salt thereof. In another embodiment of the combination composition, the NSAID is a racemic ibuprofen, or a pharmaceutically acceptable salt thereof.

In one embodiment of the combination compositions, the antihistamine is an $H_1$-receptor antagonist antihistamine, such as a diphenhydramine, a loratadine, a desloratadine, a meclizine, a quetiapine, a fexofenadine, a pheniramine, a cetirizine, a promethazine, a chlorpheniramine, a levocetirizine, or a pharmaceutically acceptable salt thereof. In one embodiment, the antihistamine is a chlorpheniramine, or a pharmaceutically acceptable salt thereof.

In one embodiment of the combination composition, the antihistamine is a chlorpheniramine, or a pharmaceutically acceptable salt thereof, and the NSAID is a racemic ibuprofen, or a pharmaceutically acceptable salt thereof.

In one embodiment, an analgesic dosage unit includes about 600 mg of a racemic ibuprofen, or a therapeutically equivalent amount of a pharmaceutically acceptable salt thereof, and an antihistamine. In one embodiment, the dosage unit is substantially free of an additional an active agent (e.g. a synthetic active agent). In one embodiment, the antihistamine is a chlorpheniramine, or a pharmaceutically acceptable salt thereof. In one embodiment, the dosage unit includes about 4 mg of chlorpheniramine, or a therapeutically equivalent amount of a pharmaceutically acceptable salt thereof.

In one embodiment, a combination composition is provided which includes: (i) a first oral dosage unit including about 600 mg of an ibuprofen, or a therapeutically equivalent amount of a pharmaceutically acceptable salt thereof; and (ii) a second oral dosage unit including an antihistamine. The combination composition may be substantially free of an additional active agent (e.g. a synthetic active agent). In some embodiments, the antihistamine is a chlorpheniramine, or a pharmaceutically acceptable salt thereof. In another embodiment, the second oral dosage unit includes about 4 mg of the chlorpheniramine, or a therapeutically equivalent amount of a pharmaceutically acceptable salt thereof.

In some embodiments, the combination composition includes co-packaged individual tablets of ibuprofen (200 or 400 mg) and chlorpheniramine maleate (2 or 4 mg). In related embodiments, the route of administration is oral. Therefore, the combination composition may include an oral combination composition dosage units (e.g. tablets). Dosing may be every 4 hours for the 200 mg ibuprofen regimen and every 8 hours for the 400 mg regimen.

B. Pharmaceutical Formulation

The combination composition can further include one or more pharmaceutically acceptable excipients. A "pharmaceutically acceptable excipient" includes pharmaceutically and physiologically acceptable, organic or inorganic carrier substances suitable for enteral or parenteral administration that do not deleteriously react with the active agent. A "pharmaceutically acceptable excipient," as used herein, excludes active agents. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinyl pyrrolidone. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the active agent.

The combination composition may include, for example, a mixture of an analgesic (e.g. NSAID), an antihistamine, and one or more pharmaceutically acceptable excipients. The mixture can be compressed into a tablet or filled into a capsule shell.

In another embodiment, the pharmaceutical formulation may contain two mixtures: a first mixture including an analgesic (e.g. NSAID) and one or more pharmaceutically acceptable excipients, and a second mixture including an antihistamine and one or more pharmaceutically acceptable excipients. The two mixtures can be compressed together (e.g., to form a tablet having a bi-layer or core/coat structure). Alternatively the two mixtures can be individually compressed to form separate analgesic (e.g. NSAID) dosage units and antihistamine dosage units.

In the pharmaceutical formulations described herein, the active agents may be in physical contact with one another (e.g., in admixture). Alternatively, the active agents may by physically separated (e.g., by coating granules of one or both active agents with a barrier coating before mixing, or by a barrier layer between tablet layers). In one embodiment, only one portion or layer of the dosage form contains active agent(s). In one embodiment, the active agent(s) is present as a uniform mixture. In another embodiment, more than one portion or layer of the dosage form contains active agent(s).

The combination composition can be formulated for any route of administration, including enteral, oral, sublingual, buccal, parenteral, intravenous, and topical routes. In one embodiment, the combination composition is formulated for oral administration.

The pharmaceutically acceptable carrier can be either solid or liquid. Solid form preparations include powders, tablets (including chewable tablets), pills, capsules, cachets, suppositories, and dispersible granules. A solid carrier may also act as a diluent, flavoring agent, binder, preservative, tablet disintegrating agent, or encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage units suitable for oral administration.

Liquid oral formulations, e.g., aqueous suspensions, can be prepared by dissolving the active agent in water and adding suitable colorants, flavors, stabilizers, and thickening agents as desired. Aqueous suspensions suitable for oral use can be made by dispersing the finely divided active agent in water with viscous material, such as natural or synthetic gums, resins, methylcellulose, sodium carboxymethylcellulose, and other well-known suspending agents.

In one embodiment, the analgesic (e.g. OTC analgesic) and/or the antihistamine is formulated as an oral dosage form, e.g., tablet, caplet, capsule, softgel, or oral suspension. In another embodiment, the analgesic (e.g. OTC analgesic) and/or the antihistamine is formulated as a tablet, caplet, capsule, or softgel (a liquid formulation encapsulated by a soft gelatin shell). In yet another embodiment, the analgesic (e.g. OTC analgesic) and/or the antihistamine is formulated as a solid oral unit dosage form.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Active agents may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose, chondroitin sulfate and salts thereof, hyaluronic acid and salts thereof, and combinations of the foregoing. Such agents are typically employed at a level between about 0.01% and about 2% by weight.

In one embodiment, the analgesic (e.g. OTC analgesic) is formulated for immediate release. In another embodiment, the antihistamine is formulated for immediate release. In another embodiment, both active agents are formulated (together or separately) for immediate release.

In other embodiments, the pharmaceutical formulations may additionally include components to provide modified, sustained, extended, delayed, or pulsatile release. Release modification can be achieved by release-modifying coatings and/or matrices. Exemplary components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

C. Dosage and Administration

The combination composition is prepared in a dose that is therapeutically effective to treat sunburn. In one embodiment, the combination composition includes a combined therapeutically effective amount of the analgesic (e.g. OTC analgesic) and antihistamine. In this case, the dosage of one active agent may be insufficient to treat a sunburn in the absence of the second active agent, but together they are therapeutically effective. In one embodiment, the analgesic (e.g. OTC analgesic) dose is therapeutically insufficient without co-administration of the antihistamine. In another embodiment, the antihistamine dose is therapeutically insufficient without co-administration of the analgesic (e.g. OTC analgesic).

In another embodiment, one or both active agents (i.e. the analgesic and the antihistamine) are present in an individually therapeutically effective amount. In this case, one or both active agents are present in an amount that is sufficient to treat sunburn, but the therapeutic effect is increased or synergistically enhanced by administering both active agents. In one embodiment, the combination composition includes an individually therapeutically effective amount of an analgesic (e.g. OTC analgesic). In another embodiment, the combination composition includes an individually therapeutically effective amount of an antihistamine. In yet another embodiment, the combination composition includes both an individually therapeutically effective amount of an analgesic (e.g. OTC analgesic) and an individually therapeutically effective amount of an antihistamine.

The appropriate dose, frequency, and duration can be modified to address the particular needs of a particular subject by taking into account factors including, but not limited to, the age, gender, weight, and health of the subject; the severity, extent (e.g., surface area), and location of the burn; and the duration of, and time elapsed since UV exposure.

In the combination compositions described herein, the analgesic (e.g. OTC analgesic) may be present in a dose amount approved for administration by the FDA (e.g. OTC administration), or it may be present in a dose amount that is higher or lower than an FDA approved dose for administration (e.g. OTC administration). In some embodiments, the analgesic (e.g. OTC analgesic) is present in a dose amount that is equal to an FDA-approved dose (e.g. OTC dose). In yet another embodiment, the analgesic (e.g. OTC analgesic) is present in a dose amount that is within the range of FDA-approved doses (e.g. OTC doses). In some embodiments, the analgesic (e.g. OTC analgesic) dose amount is more than 75%, at least 100%, or more than 100% of an FDA-approved dose (e.g. OTC dose). The FDA-approved doses referred to in this paragraph are those approved as of Oct. 26, 2009.

In some embodiments, the analgesic is acetaminophen. The acetaminophen dose amount may be about 100 mg to about 4000 mg, about 80 mg to about 160 mg, about 325 mg to about 650 mg, about 325 mg to about 500 mg, or about 500 mg to about 1000 mg. In some embodiments, the acetaminophen dose is about 325 mg, about 500 mg, or about 650 mg. In some embodiments, the acetaminophen daily dose is about 100 mg to about 4000 mg, about 325 mg to about 500 mg, about 650 mg to about 1000 mg, or about 975 mg to about 1500 mg.

In some embodiments, the analgesic is an NSAID. The NSAID (e.g. ibuprofen) dose amount may be about 50 mg to about 800 mg, about 50 mg to about 600 mg, about 200 mg to about 600 mg, about 200 mg to about 400 mg, or about 50 mg, about 100 mg, about 150 mg, about 200 mg, about 250 mg, about 300 mg, about 350 mg, about 400 mg, about 450 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg. In another embodiment, the amount of NSAID is about 50 mg, about 100 mg, about 200 mg, about 400 mg, or about 600 mg. In one embodiment, the NSAID dose is about 100 mg ibuprofen, 150 mg ibuprofen, about 200 mg ibuprofen, about 250 mg ibuprofen, about 300 mg ibuprofen, about 350 mg ibuprofen, about 400 mg ibuprofen, about 450 mg ibuprofen, about 500 mg ibuprofen, about 550 mg ibuprofen, about 600 mg ibuprofen, about 650 mg ibuprofen, about 700 mg ibuprofen, about 750 mg ibuprofen, about 800 mg ibuprofen, about 850 mg ibuprofen, about 900 mg ibuprofen, about 950 mg ibuprofen, or about 1000 mg ibuprofen. In one embodiment, the NSAID dose is about 200 mg ibuprofen. In another embodiment, the NSAID dose is about 400 mg ibuprofen. In another embodiment, the NSAID dose is about 600 mg ibuprofen. In one embodiment, the NSAID dose is about 600 mg of racemic ibuprofen, or a therapeutically equivalent amount of a pharmaceutically acceptable salt thereof.

The NSAID dose amount may be present in a single dosage unit, or it may be divided among more than one dosage unit. For example, in one embodiment, the combination composition includes an NSAID dosage unit containing about 200 mg ibuprofen. In another embodiment, the NSAID dosage unit contains about 400 mg ibuprofen. In yet another embodiment, the NSAID dosage unit contains about 600 mg ibuprofen. In some embodiments, the NSAID daily dose is about 50 mg to about 3200 mg, about 50 mg to about 2000 mg, about 200 mg to about 1800 mg, about 400 mg to about 1600 mg, about 600 mg to about 1200 mg, or about 200 mg, about 400 mg, about 600 mg, about 800 mg, or about 1000 mg per 24 hours. These exemplary NSAID amounts are particularly suitable when the NSAID is ibuprofen. Adjustments may be made as necessary for various salt forms or alternative NSAIDs.

In some embodiments, the antihistamine (e.g. chlorpheniramine) dose amount is about 1 mg to about 10 mg, about 1 mg to about 8 mg, about 2 mg to about 8 mg, about 2 mg to about 6 mg, about 2 mg to about 4 mg, or about 2 mg, about 4 mg, about 6 mg, or about 8 mg. In one embodiment, the antihistamine dose is about 1 mg, about 2 mg, about 3 mg, about 4 mg, about 5 mg, about 6 mg, about 7 mg, about 8 mg, about 9 mg, about 10 mg chlorpheniramine. In one embodiment, the antihistamine dose is about 2 mg chlorpheniramine. In another embodiment, the antihistamine dose is about 4 mg chlorpheniramine. In yet another embodiment, the antihistamine dose is about 6 mg chlorpheniramine. In yet another embodiment, the antihistamine dose is about 8 mg chlorpheniramine. In some embodiments, the antihistamine dose amount is more than 75%, at least 100%, or more than 100% of an FDA approved dose (e.g. OTC dose) as of Oct. 26, 2009.

The antihistamine dose amount may be present in a single dosage unit, or it may be divided among more than one dosage unit. In some embodiments, the antihistamine daily dose is about 2 mg to about 50 mg, about 2 mg to about 24 mg, about 2 mg to about 16 mg, or about 2 mg to about 8 mg, about 2 mg, about 4 mg, about 6 mg, about 8 mg, about 10 mg, about 12 mg, about 14 mg, or about 16 mg per 24 hours. These exemplary amounts are particularly suitable when the antihistamine is chlorpheniramine. One of ordinary skill in the art could adjust as necessary for various salt forms or alternative antihistamines.

In one embodiment, the combination composition includes about 50, 200, 400, 600, or 800 mg of ibuprofen and about 2, 4, 6 or 8 mg chlorpheniramine. In another embodiment, the combination composition includes about 200, 400, or 600 mg of ibuprofen and about 2, 4, or 8 mg chlorpheniramine. In another embodiment, the combination composition includes about 200 or 400 mg ibuprofen and about 2 or 4 mg chlorpheniramine. In another embodiment, the combination composition includes about 200 mg ibuprofen and about 2 mg chlorpheniramine. In another embodiment, the combination composition includes about 400 mg ibuprofen and about 4 mg chlorpheniramine. In another embodiment, the combination composition includes about 600 mg ibuprofen and about 4 mg chlorpheniramine. In yet another embodiment, the combination composition includes about 200 mg ibuprofen and about 4 mg chlorpheniramine. In yet another embodiment, the combination composition includes about 400 mg ibuprofen and about 2 mg chlorpheniramine.

In some embodiments, the combination composition is administered about every 24, 23, 22, 21, 20, 19, 18, 17, 16, 15, 14, 13, 12, 11, 9, 8, 7, 6, 5, 4, 3, 2 or 1 hour(s). In one embodiment, the combination composition is administered about every 24, 12, 8, 6, or 4 hours. In yet another embodiment, the combination composition is administered every 8 or 12 hours. In some embodiments, the combination composition is administered 2, 3, 4, 5, or 6 times during at least one 24 hour period. In another embodiment, the combination composition is administered 2 or 3 times during at least one 24 hour period. In some embodiments, the combination composition is administered two times per day (BID), three times per day (TID), four times a day (QID), five time per day, or six times per day.

In some embodiments, administration of the combination composition includes simultaneous or approximately simultaneous administration of both active agents, whether co-formulated or individually formulated. However, staggered administration is also contemplated, whereby at least one dose of an active agent is administered sequentially. For example, one active agent may be administered once a day, while the other active agent is administered twice a day.

A staggered dosing regimen is exemplified by FIG. 4. A staggered dosing regimen can include administering a combination of an analgesic (e.g. OTC analgesic) and antihistamine, and administering an optional follow up dose of an analgesic (e.g. OTC analgesic). Thus, the analgesic (e.g. OTC analgesic) may be administered more frequently (e.g., twice as frequently) as the antihistamine. The combination dose may be separately formulated and co-administered (as pictured) or co-formulated (not shown). The following table describes an exemplary staggered dosing schedule for one day (t=0-24 hours). In one embodiment, the dosing regimen is administered for 1, 2, 3, or 4 days.

TABLE 1

QID Staggered Dosing

| Schedule | Time (h) | Dose |
|---|---|---|
| 8 am | 0 | N (200 mg) |
| | | AH (2 to 4 mg) |
| 10 am | 2 | N (100 mg) |
| 12 pm | 4 | N (200 mg) |
| | | AH (2 to 4 mg) |
| 2 pm | 6 | N (100 mg) |
| 4 pm | 8 | N (200 mg) |
| | | AH (2 to 4 mg) |
| 6 pm | 10 | N (100 mg) |
| 8 pm | 12 | N (200 mg) |
| | | AH (2 to 4 mg) |
| 10 pm | 14 | N (100 mg) |

N = analgesic (e.g. OTC analgesic);
AH = antihistamine

In one aspect, the combination composition is administered over a sufficient number of days to treat the sunburn of a subject. In some embodiments, the combination composition is administered for 1, 2, 3, 4, 5, 6, or 7 days, preferably consecutive days. In another embodiment, the combination composition is administered for 2 to 6 days. In another embodiment, the combination composition is administered for 2 to 5 days. In another embodiment, the combination composition is administered for 3 to 5 days. In another embodiment, the combination composition is administered for 3 to 4 days. In another embodiment, the combination composition is administered for at least 3 consecutive days. In another embodiment, the combination composition is administered for at least 2 consecutive days. In another embodiment, the combination composition is administered for no more than 3 consecutive days. In another embodiment, the combination composition is administered for no more than 2 consecutive days.

The combination composition can be provided as a combination product including a plurality of analgesic (e.g., NSAID) doses and a plurality of antihistamine doses. In some embodiments, the combination product can include co-formulated active agents. For example, the product may include a plurality of combination dosage units, wherein the combination dosage unit contains both an NSAID and an antihistamine. In other embodiments, the combination product includes individually formulated active agents. For example, the product can include a plurality of NSAID dosage units (containing an NSAID but no antihistamine) and a plurality of antihistamine dosage units (containing an antihistamine but no NSAID.) In any of these embodiments, the combination product can be substantially free of any additional active agent, any additional oral active agent, any additional synthetic active agent, and/or any additional active agent for treating sinus symptoms.

In one embodiment, the analgesic (e.g., NSAID) dosage units and the antihistamine dosage units are visibly distinguishable by size, shape, color, etc.

In one embodiment, the number of analgesic (e.g., NSAID) doses and the number of antihistamine doses are independently selected from a minimum of 3 to a maximum of 40, about 3 to about 6, about 18 to about 36, about 6 to about 12, about 9 to about 18, about 16 to about 20, or about 18 doses. The number of analgesic (e.g., NSAID) doses may be the same as or different from the number of the antihistamine doses. In one embodiment, the number of analgesic (e.g., NSAID) doses is the same as the number of the antihistamine doses. In one embodiment, the analgesic (e.g., NSAID) doses and the antihistamine doses are co-formulated. In another embodiment, the analgesic (e.g., NSAID) doses and the antihistamine doses are co-administered.

In another embodiment, the number of analgesic (e.g., NSAID) dosage units and the number of antihistamine dosage units are independently selected from a minimum of 3 to a maximum of 40, about 3 to about 6, about 18 to about 36, about 6 to about 12, about 9 to about 18, about 16 to about 20, or about 18 dosage units. The number of analgesic (e.g., NSAID) dosage units may be the same as or different from the number of the antihistamine dosage units. In one embodiment, the number of analgesic (e.g., NSAID) dosage units is the same as the number of the antihistamine dosage units. In another embodiment, the combination product provides a dose including two analgesic (e.g., NSAID) dosage units and one antihistamine dosage unit.

In one embodiment, the oral combination composition includes: (i) 16-20 analgesic (e.g., ibuprofen) dosage units, each containing about 50 mg to about 800 mg of ibuprofen, or a pharmaceutically acceptable salt thereof; and (ii) 16-20 chlorpheniramine dosage units, each containing about 1 mg to about 8 mg of chlorpheniramine, or a pharmaceutically acceptable salt thereof, wherein the dosage units are suitable for administering 2-6 times per day, and wherein the analgesic (e.g., ibuprofen) oral dosage units and the chlorpheniramine oral dosage units are substantially free of an additional synthetic active agent.

In another embodiment, the oral combination composition includes: 16-20 dosage units, each containing about 50 mg to about 800 mg of analgesic (e.g., ibuprofen) and about 1 mg to about 8 mg of chlorpheniramine, wherein the dosage units are suitable for administering 3-6 times per day, and wherein said oral dosage units are substantially free of an additional synthetic active agent.

In another embodiment, the oral combination composition includes: a minimum of 3 and a maximum of 40 oral dosage units, wherein each oral dosage unit comprises an OTC analgesic (e.g., NSAID) dose and an antihistamine dose, wherein the oral dosage units are substantially free of an additional synthetic active agent.

In yet another embodiment, the oral combination composition includes: (i) a minimum of 3 and a maximum of 40 analgesic (e.g., NSAID) oral dosage units, wherein each analgesic (e.g., NSAID) oral dosage unit comprises a dose of an analgesic (e.g., NSAID); and (ii) a minimum of 3 and a maximum of 40 antihistamine oral dosage units, wherein each antihistamine oral dosage unit comprises a dose of an antihistamine, wherein the analgesic (e.g., NSAID) and antihistamine oral dosage units are substantially free of an additional synthetic active agent. In one embodiment, the oral combination composition product includes: (i) a minimum of 4 and a maximum of 32 non-steroidal anti-inflammatory drug oral dosage units; and (ii) a minimum of 4 and a maximum of 16 antihistamine oral dosage units. In another embodiment, the oral combination composition product includes: (i) a minimum of 4 and a maximum of 16 non-steroidal anti-inflammatory drug oral dosage units each comprising about 200 mg ibuprofen; (ii) a minimum of 4 and a maximum of 16 antihistamine oral dosage units each comprising 2-4 mg chlorpheniramine; and (iii) a minimum of 4 and a maximum of 16 non-steroidal anti-inflammatory drug oral dosage units each comprising about 100 mg ibuprofen.

In one embodiment, the oral combination composition includes: (i) a first oral dosage unit comprising about 600 mg of an analgesic (e.g., ibuprofen), or a therapeutically equivalent amount of a pharmaceutically acceptable salt thereof; and (ii) a second oral dosage unit comprising an antihistamine.

The dosage ranges provided herein are inclusive of the recited numbers. The term "about" as used herein is inclusive of, and in some embodiments equal to, the recited number.

III. Kits Including the Combination Composition

In one aspect, the combination composition is provided as part of a kit to facilitate a suitable dosing regimen for treating sunburn. The combination composition ad embodiments thereof are described above and are equally applicable to the kits provided herein. The kits can further include a dispensing apparatus configured to facilitate suitable administration, suitable frequency, and/or suitable duration of treatment. The suitability of the dispensing apparatus may be based partly or completely on the combination composition. Thus, the kit may include a dispensing apparatus having a plurality of analgesic dosage units and a plurality of antihistamine dosage units (e.g. combination compositions).

In some embodiments, the kit includes a dispensing apparatus including a plurality of analgesic dosage units (e.g. oral dosage units, parenteral dosage unites or topical dosage units) and a plurality of antihistamine dosage units (e.g. oral dosage units, parenteral dosage unites or topical dosage units). The number of analgesic dosage units is equal to the number of antihistamine oral dosage units. The dosage units are substantially free of an additional synthetic active agent. The dispensing apparatus is configured to dispense, 2 to 6 times daily over not more than a three day period, one or two analgesic oral dosage units (e.g. OTC analgesics dosage units) and one or two antihistamine oral dosage units approximately simultaneously, or one or two analgesic dosage units (e.g. oral dosage units, parenteral dosage unites or topical dosage units) and one or two antihistamine dosage unites (e.g. oral dosage units, parenteral dosage unites or topical dosage units) sequentially.

In one embodiment of the kit, the analgesic is an NSAID (e.g. ibuprofen). The antihistamine may be chlorpheniramine. In another embodiment, the analgesic is an OTC analgesic. The dosage units may be oral dosage units.

The dispensing apparatus can include any packaging, overwrap, or reusable structure such as a bottle, canister, packeting (e.g., of the type used to dispense Vitapak®), blister pack (e.g., unit or dose dispensing blister packs), snap-lid type dispenser (e.g., of the type used for weekly pill organizers), automated dispensers (such as those manufactured by ePill), etc.

In one embodiment, the dispensing apparatus is configured to dispense individual dosage units (e.g., tablets). In another embodiment, the dispensing apparatus is configured to dispense a dose, which may include more than one dosage unit. In another embodiment, the dispensing apparatus is configured to dispense a daily dose, which may include more than one dose. In another embodiment, the dispensing apparatus is configured to dispense doses for the duration of treatment. The dispensing apparatus can optionally include one or more partitions, perforations, or markings, etc. to compartmentalize dosage units, active agents, single doses, daily doses, and/or treatment periods. The dispensing apparatus can be configured to dispense adult doses only, pediatric doses only, or to be capable of dispensing adult and/or pediatric doses depending on the administration regimen.

Figure 2B:
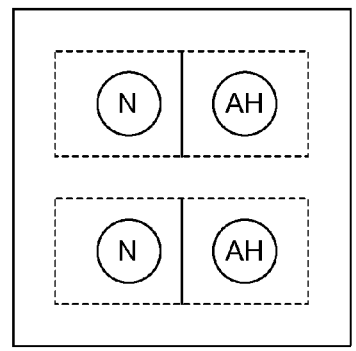
Figure 2C:
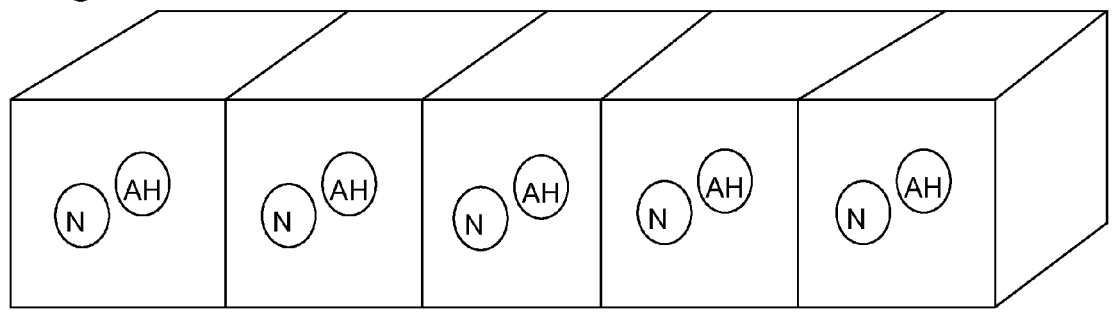

In some embodiments, the dispensing apparatus is configured to facilitate co-administration of both an analgesic (e.g., NSAID) and an antihistamine. The dispensing apparatus can be, for example, a dispensing mechanism that ejects both active agents at once. For example, the dispensing apparatus can be a blister pack having combination blisters. A combination blister may eject both active agents approximately simultaneously, whether formulated together or separately. For example, each blister can contain both an NSAID dosage unit and an antihistamine dosage unit. Alternatively, each blister could contain a combination dosage unit containing both the NSAID and the antihistamine. In either case, dispensing one active agent would also dispense the second active agent. (See FIG. 2.) The combination blister may optionally include a partition to compartmentalize an NSAID dosage unit and an antihistamine dosage unit to prevent interaction, friction, or other degradation during transport.

Figure 5A:
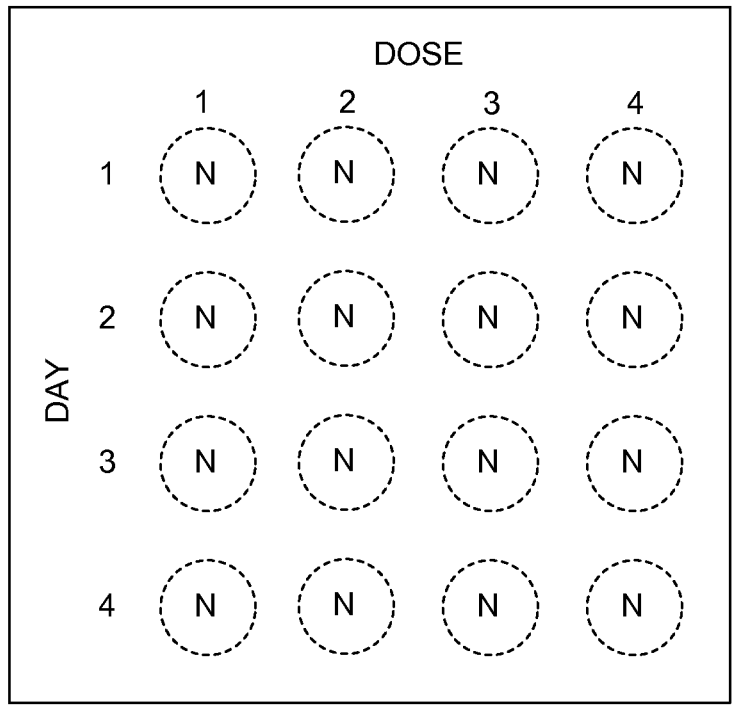
FIGS. 5A-5B depict kits including two blister packs: a first blister pack for dispensing an OTC analgesic (FIG. 5A), and a second blister pack for dispensing an antihistamine (FIG. 5B). The first and second blister packs are distinguishable within the kit by, e.g., shading as shown. This exemplary kit features QID dosing for 4 days.
Figure 5B:
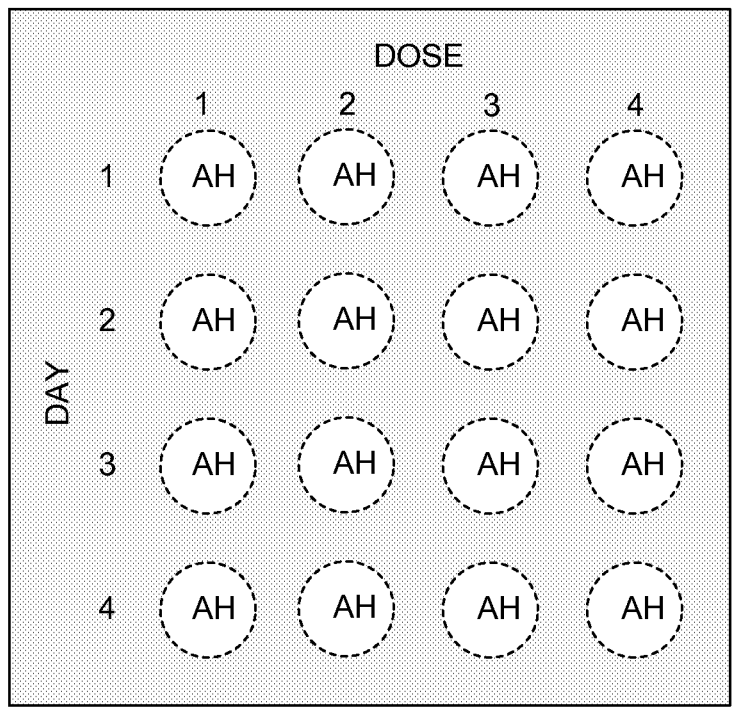

In another embodiment, the kit or dispensing apparatus can eject the active agents separately. In one embodiment, each active agent is contained in an independent blister pack with detailed instructions for combined dosing (FIG. 5). In another embodiment, each blister contains one active agent, but the blister pack contains both active agents. This dispensing apparatus preferably includes one or more partitions, perforations, or markings to encourage co-administration of both active agents. For example, the dispensing apparatus can be a blister pack wherein each active agent is confined within a distinct blister, but the blisters are aligned, grouped, or otherwise configured to encourage the subject to dispense both active agents (or otherwise indicate to the subject that both active agents should be co-administered). For example, the blisters can be clustered in groups including at least one NSAID blister containing an NSAID and at least one antihistamine blister containing an antihistamine. The blisters can be arranged (e.g., in rows and columns), partitioned, perforated, or marked to designate individual doses, daily doses, or treatment regimens. (See FIG. 1.)

Figure 3:
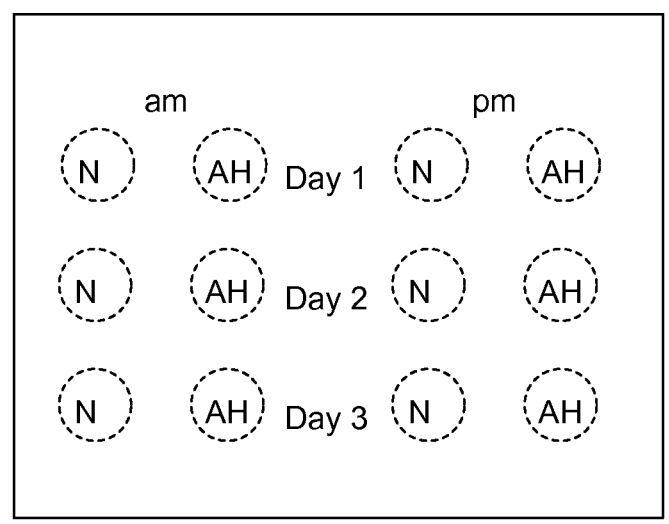
FIG. 3 depicts an exemplary dispenser configuration featuring indications (text and perforations) for BID dosing and a treatment duration of 3 days.

In some embodiments, the dispensing apparatus can be configured to facilitate suitable frequency of duration. The dispensing apparatus can include text, label, configuration, size, shape, marking, perforation, or other indicator to facilitate a suitable frequency of duration (e.g., 2-6 doses of the combination composition within a 24 hour period). (See FIG. 3.) This can be accomplished by providing a single package containing doses for a single 24 hour period, or it can be accomplished by marking or perforating the package to indicate the daily dose of the combination composition.

In some embodiments, the dispensing apparatus can be configured to facilitate suitable duration of treatment. The dispensing apparatus can include text, label, configuration, size, shape, marking, perforation, or other indicator to facilitate an entire treatment regimen (e.g., including the doses for 3 to 6 days as described above). This can be accomplished by providing a single package containing doses for the entire treatment period (see FIG. 3), or it can be accomplished by marking or perforating the package to indicate the treatment dose of the combination composition.

The dispensing apparatus may also be configured to dispense one or two first oral dosage units and one or two second oral dosage units approximately simultaneously, or one or two first oral dosage units and one or two second oral dosage units sequentially.

In some embodiments, the kit includes a blister pack and the combination composition. Thus, the dispensing apparatus may be a blister pack.

In one embodiment, the blister pack includes at least one analgesic (e.g., NSAID) blister and at least one antihistamine blister, preferably a plurality of NSAID blisters and a plurality of antihistamine blisters. In one embodiment, each blister contains a single dosage unit. In one embodiment, the number of analgesic (e.g. NSAID) blisters and the number of antihistamine blisters are independently selected from about 4 to about 24, about 6 to about 20, about 10 to about 20, about 16 to about 20, or about 18 blisters. In one embodiments, the number of analgesic (e.g. NSAID) blisters and the number of antihistamine blisters are the same.

In another embodiment, the blister pack includes at least one combination blister, preferably a plurality of combination blisters. The number of combination blisters can be about 1 to about 40, about 3 to about 6, about 18 to about 36, about 6 to about 12, about 9 to about 18, about 16 to about 20, or about 18 blisters.

In one embodiment, the kit includes 18 analgesic (e.g. NSAID) blisters and 18 antihistamine blisters. In some embodiments, each analgesic blister contains a 200 mg ibuprofen oral dosage form. In some embodiments, each antihistamine blister contains 2 mg chlorpheniramine. In other embodiments, the kit includes 18 analgesic (e.g. NSAID) and 18 antihistamine combination blisters. In some related embodiments, the kit includes 18 combination blisters each containing 200 mg ibuprofen and 2 mg chlorpheniramine.

In one embodiment, the kit includes 18 analgesic (e.g. NSAID) blisters and 18 antihistamine blisters. In some embodiments, each analgesic blister contains a 200 mg or 400 mg ibuprofen oral dosage form. In some embodiments, each antihistamine blister contains 2 mg or 4 mg chlorpheniramine. In other embodiments, the kit includes 18 analgesic (e.g. NSAID) and 18 antihistamine combination blisters. In some related embodiments, the kit includes 18 combination blisters each containing 200 mg or 400 mg ibuprofen and 2 mg or 4 mg chlorpheniramine.

The kit may further include text, label, configuration, size, shape, marking, perforation, or other indicator to facilitate the administration of 1-2 analgesic (e.g. NSAID) dosage units and 1-2 antihistamine dosage units approximately simultaneously. The kit may further include text, label, configuration, size, shape, marking, perforation, or other indicator to facilitate dosing about every 4-12, 4-8, 4-6, or about 4 hours. Likewise, the kit may further include text, label, configuration, size, shape, marking, perforation, or other indicator to facilitate dosing two times per day (BID), three times per day (TID), four times a day (QID), five time per day, or six times per day. The kit may further include text, label, configuration, size, shape, marking, perforation, or other indicator to facilitate dosing for about 3 to about 6 days, preferably about 3 consecutive days.

IV. Methods of Treating Sunburns

Methods of treating a sunburn in a subject, particularly a human subject, in need of such treatment, are also provided. The method includes administering to the subject a combined therapeutically effective amount of an analgesic (e.g., NSAID) and an antihistamine. The analgesic and antihistamine may be administered as a combination composition as described above. Thus, the combination compositions described above, including all embodiments thereof, are equally useful for the methods provided herein.

In one embodiment, there is provided a method of treating a sunburn in a subject, e.g., a human subject, in need of such treatment which includes administering to the subject a combined therapeutically effective amount of an analgesic and an antihistamine.

In one embodiment, the analgesic (e.g. OTC analgesic) is acetaminophen or an NSAID. In another embodiment, the OTC analgesic is an NSAID. In another embodiment, the NSAID is an aspirin, an ibuprofen, a naproxen, or a pharmaceutically acceptable salt thereof. In one embodiment, the NSAID is an ibuprofen, or a pharmaceutically acceptable salt thereof.

The antihistamine may be an H1-receptor antagonist antihistamine. The H1-receptor antagonist antihistamine may be a diphenhydramine, a loratadine, a desloratadine, a meclizine, a quetiapine, a fexofenadine, a pheniramine, a cetirizine, a promethazine, a chlorpheniramine, a levocetirizine, or a pharmaceutically acceptable salt thereof. In one embodiment, the antihistamine is a chlorpheniramine, or a pharmaceutically acceptable salt thereof.

The antihistamine and analgesic (e.g. combination composition) may be administered after the subject is exposed to UV radiation. Exemplary sources of UV radiation include, but are not limited to, natural sources such as sunlight, and artificial sources such as lasers, lamps, and tanning booths (e.g. natural sunlight or solar simulator). In one embodiment, the subject has been exposed to natural sunlight. In some embodiments, the duration of UV exposure is more than about 5 minutes, 10 minutes, 15 minutes, 30 minutes, 45 minutes, 60 minutes, 2 hours, 5 hours, or 10 hours. Thus, administering may be performed after exposure of the subject to ultraviolet radiation, e.g., after at least 0.25, 0.5, 1, 2, 3, 4, 5, 6, 7, 8, 10, 12, 18, 24 hours, or even longer. In some embodiments, the administering is at least about 1, 2, 3, 5, 8, 10, 12, 24, or 48 hours after UV exposure. The administering may also be about 3 to about 5 hours after UV exposure (e.g. natural sunlight exposure leading to sunburn). The administering may also be performed at least two hours after exposure of the subject to ultraviolet radiation.

In another embodiment, the administering is performed after appearance of one or more symptom(s) of sunburn in the subject. Exemplary burn symptoms include, but are not limited to, erythema (redness), pain, edema (swelling), itching, peeling, rash, blistering, warmth, nausea, headache, and fever.

The term "sunburn" is used herein according to its generally accepted meaning in the art. A sunburn to skin is understood to result from overexposure to ultraviolet (UV) radiation. In one embodiment, the sunburn is a first degree burn. In another embodiment, the subject in need of treatment has a sunburn that is a superficial (extending to the papillary dermis) or deep (extending to the reticular dermis) second degree burn. In yet another embodiment, the subject in need of treatment has sunburn that is a third degree burn. In another embodiment, the subject has a sunburn that is a fourth degree burn. For more severe burns (third and fourth degree), parenteral routes (e.g., IV) of administration may be desirable on an in-patient or out-patient basis. Thus, in some embodiments, the sunburn is an acute sunburn. The term "acute sunburn" is used according to its generally understood meaning in the art.

In some embodiments, the administering is conducted about every 24, 23, 22, 21, 20, 19, 18, 17, 16, 15, 14, 13, 12, 11, 9, 8, 7, 6, 5, 4, 3, 2 or 1 hour(s). In one embodiment, the administering is about every 24, 12, 8, 6, or 4 hours. In yet another embodiment, the administering is about every 8 or 12 hours. In some embodiments, the administering is about 2, 3, 4, 5, or 6 times during at least one 24 hour period. In another embodiment, the administering is about 2 or 3 times during at least one 24 hour period. In some embodiments, the administering is two times per day (BID), three times per day (TID), four times a day (QID), five time per day, or six times per day.

In one embodiment, the administering is orally administering. In another embodiment, the administering is topically administering. In another embodiments, the administering is parenterally administering.

In one embodiment, the method includes orally administering at least one active agent. In another embodiment, the method includes orally administering both the analgesic (e.g., NSAID) and the antihistamine. In other embodiments, the antihistamine and/or analgesic are/is topically administered.

In some embodiments, the method of treating a sunburn in a subject is a method of decreasing recovery time from a sunburn. In some embodiments, the method of treating a sunburn in a subject is a method of relieving pain (e.g. temporarily) and/or relieving discomfort (e.g. temporarily) resulting form a sunburn (e.g. a mild to moderate or acute sunburn). In some embodiments, the method of treating a sunburn in a subject is a method of relieving redness (e.g. temporarily) in the skin of a subject resulting from a sunburn (e.g. a mild to moderate or acute sunburn).

Pain and comfort may be assessed using known means in the art such as by using a visual analog scale (VAS) method. The efficacy of the combination compositions may be determined by comparing the pain a subject reports at various time intervals after drug and/or placebo administration. Efficacy may be determined by comparing the pain reported after treatment with the combination compositions to placebo in a crossover model. Erythema may be measured using conventional means in the art. Efficacy of the combination compositions may be determined by comparing the erythema reported after treatment with the combination compositions to that after placebo treatment in a crossover model.

Several embodiments of the invention are specifically described herein. Embodiments described in one section of this application are equally applicable to all other sections of the applications where appropriate. For examples, all embodiments of the combination compositions are equally applicable to the kits and methods provided herein. Likewise, the dosages and administrations are equally applicable to the kits and methods. Moreover, for example, embodiments of the kits are equally applicable to the methods and vice versa.

The disclosures of all references and publications cited above are expressly incorporated by reference in their entireties to the same extent as if each were incorporated by reference individually.

To further illustrate particular embodiments, the following non-limiting examples are provided.

EXAMPLES

Example 1

Combination Composition for Treating Sunburn

Combination compositions were prepared including ibuprofen as the over-the-counter analgesic and chlorpheniramine as the antihistamine. The combination compositions were prepared according to the following dosage levels:

TABLE 2

| Combination Composition Dosages | | |
|---|---|---|
| Dosage | Chlorpheniramine (mg) | Ibuprofen (mg) |
| D1 | 4 | 200 |
| D2 | 4 | 400 |
| D3 | 4 | 600 |
| D4 | 2 | 600 |
| D5 | 4 | 800 |
| D6 | 8 | 800 |

The active agents were individually formulated, but administered simultaneously or nearly simultaneously.

Example 2

Study Demonstrating Efficacy in Treating Sunburn

Each of the combination composition dosages described in the preceding Example was administered to at least one volunteer to assess its efficacy in treating sunburn. The results are provided in the following table.

The average time to first reported onset of relief was about 45 minutes at each dosage level. Notably, each subject reported complete recovery in no more than 3 days.

TABLE 3

| | | | | | | | | | | | | | | After Treatment Assessment | | |
|---|---|---|---|---|---|---|---|---|---|---|---|---|---|---|---|---|
| Subject Number | Age Grp | Dosage | Freq. of Dose | Complexion Type | Surface Area | Severity | Pain | Edema | Stinging & Itching | Erythema | Heat & Burn Sensation | Day 1 | Day 2 | Day 3 |
| 1 | Child | D1 | ~6 hr | F | H | S | 3+ | 3+ | 3+ | 3+ | 3+ | 2+ | 1+ | 0 |
| 2 | Child | D1 | ~6 hr | M | H | S | 3+ | 2+ | 3+ | 3+ | 2+ | 2+ | 1+ | 0 |
| 3 | Adult | D2 | ~6 hr | F | H | S | 3+ | 3+ | 3+ | 3+ | 3+ | 2+ | 1+ | 0 |
| 4 | Adult | D2 | ~6 hr | F | H | S | 3+ | 3+ | 3+ | 3+ | 3+ | 2+ | 1+ | 0 |
| 5 | Adult | D2 | ~6 hr | F | H | S | 3+ | 3+ | 3+ | 3+ | 3+ | 2+ | 1+ | 0 |
| 6 | Adult | D2 | ~6 hr | M | M | S | 3+ | 3+ | 3+ | 3+ | 3+ | 2+ | 0 | 0* |
| 7 | Adult | D2 | ~6 hr | M | M | S | 3+ | 2+ | 3+ | 3+ | 2+ | 2+ | 0 | 0* |
| 8 | Adult | D3 | ~6 hr | F | H | S | 3+ | 3+ | 3+ | 3+ | 3+ | 2+ | 1+ | 0 |
| 9 | Adult | D3 | ~6 hr | F | H | S | 3+ | 3+ | 3+ | 3+ | 3+ | 2+ | 1+ | 0 |
| 10 | Adult | D4 | ~6 hr | F | H | S | 3+ | 3+ | 3+ | 3+ | 3+ | 2+ | 1+ | 0 |
| 11 | Adult | D5 | ~6 hr | F | H | S | 3+ | 3+ | 3+ | 3+ | 3+ | 2+ | 1+ | 0 |
| 12 | Adult | D6 | ~8 hr | F | H | S | 3+ | 3+ | 3+ | 3+ | 3+ | 2+ | 1+ | 0 |
| 13 | Adult | D6 | ~8 hr | F | H | S | 3+ | 3+ | 3+ | 3+ | 3+ | 2+ | 1+ | 0 |
| 14 | Adult | D6 | ~8 hr | M | H | S | 3+ | 3+ | 3+ | 3+ | 3+ | 2+ | 1+ | 0 |

Complexion Type:
Fair (F),
Medium (M),
Dark (D).
Surface Area:
High (H) ≥75%,
Medium (M) ≥50% to ≤75%,
Low (L) ≤50%.
Severity:
S (Severe),
Moderate (Mo),
Mild (Mi).
Pain, Edema, Stinging & Itching, Erythema, and Heat & Burn Sensation:
High (3+),
Medium (2+),
Low (+).
After Treatment Assessment:
Uncomfortable (3+): inability to sleep or wear clothing and/or discomfort in daily activities;
Comfortable (2+): ability to sleep, wear clothing, and perform daily function with minimal discomfort;
Decreased sensitivity and enhanced comfort (1+);
Complete recovery (0): no pain, edema, stinging and itching, erythema, or hot and burning sensation.
*Including 2 subjects reporting complete recover on Day 2.

What is claimed is:

1. A method of treating pain or discomfort resulting from a sunburn in a subject in need of such treatment, said method comprising orally administering to said subject a combined therapeutically effective amount of ibuprofen and chlorpheniramine, or pharmaceutically acceptable salt thereof, wherein the dose amount of ibuprofen is from 50 mg to 800 mg, and the dose amount of chlorpheniramine is from 2 mg to 8 mg.

2. The method according to claim 1, wherein said combined therapeutically effective amount of ibuprofen and chlorpheniramine, or pharmaceutically acceptable salt thereof, are co-formulated to form at least a portion of a single dosage unit.

3. The method according to claim 1, wherein said combined therapeutically effective amount of ibuprofen and chlorpheniramine, or pharmaceutically acceptable salt thereof, are individually formulated to form separate dosage units.

4. The method according to claim 3, wherein said dosage units are for use in administering 2 to 6 times a day.

5. The method according to claim 1, wherein said combined therapeutically effective amount of ibuprofen and chlorpheniramine, or pharmaceutically acceptable salt thereof, are free of any additional active agent.

6. The method according to claim 1, wherein the dose amount of ibuprofen or pharmaceutically acceptable salt thereof, is from 200 mg to 400 mg, and wherein the dose amount of chlorpheniramine or pharmaceutically acceptable salt thereof is 4 mg.

* * * * *